United States Patent [19]

Lynnworth

[11] 4,286,470

[45] Sep. 1, 1981

[54] CLAMP-ON ULTRASONIC TRANSDUCER

[75] Inventor: Lawrence C. Lynnworth, Waltham, Mass.

[73] Assignee: LFE Corporation, Waltham, Mass.

[21] Appl. No.: 86,330

[22] Filed: Oct. 19, 1979

[51] Int. Cl.³ .......................................... G01N 29/00
[52] U.S. Cl. .................................. 73/861.18; 73/637
[58] Field of Search .......... 73/861.18, 861.23, 861.25, 73/861.26, 861.27, 861.28, 861.29, 861.31, 622, 632, 637, 638, 640, 597; 310/334, 336, 348, 354

[56] References Cited

U.S. PATENT DOCUMENTS

| | | | |
|---|---|---|---|
| 3,248,933 | 5/1966 | Stebbins | 310/336 |
| 3,921,440 | 11/1975 | Toth | 73/622 |
| 3,934,457 | 1/1976 | Clark et al. | 73/637 |
| 3,955,425 | 5/1976 | Corneau | 73/622 |
| 3,987,674 | 10/1976 | Baumoel | 73/861.28 |
| 4,098,117 | 7/1978 | Baumoel | 73/861.18 |

OTHER PUBLICATIONS

L. C. Lynnworth, "Industrial Applications of Ultrasound", *IEEE Sonics and Ultrasonics*, SU-22, No. 2, pp. 74-75, Mar. 1975.

*Primary Examiner*—Stephen A. Kreitman
*Attorney, Agent, or Firm*—Kenway & Jenney

[57] ABSTRACT

A clamp on ultrasonic transducer having a clamping element which can be positioned around a conduit with the inner portion of the clamping element being formed to fit closely against the outer wall of the conduit, thus defining at a selected position along the conduit a transverse reference plane. The clamping element carries on it one or more channels extending parallel to the axis of the conduit with ultrasonic transducing elements adjustably mounted on those channels such that their contact pressure with the conduit can be independently adjusted. The ultrasonic transducing elements then form a path of ultrasonic interrogation in a plane parallel to the axis of the conduit and at a position defined by the transverse reference plane.

6 Claims, 5 Drawing Figures

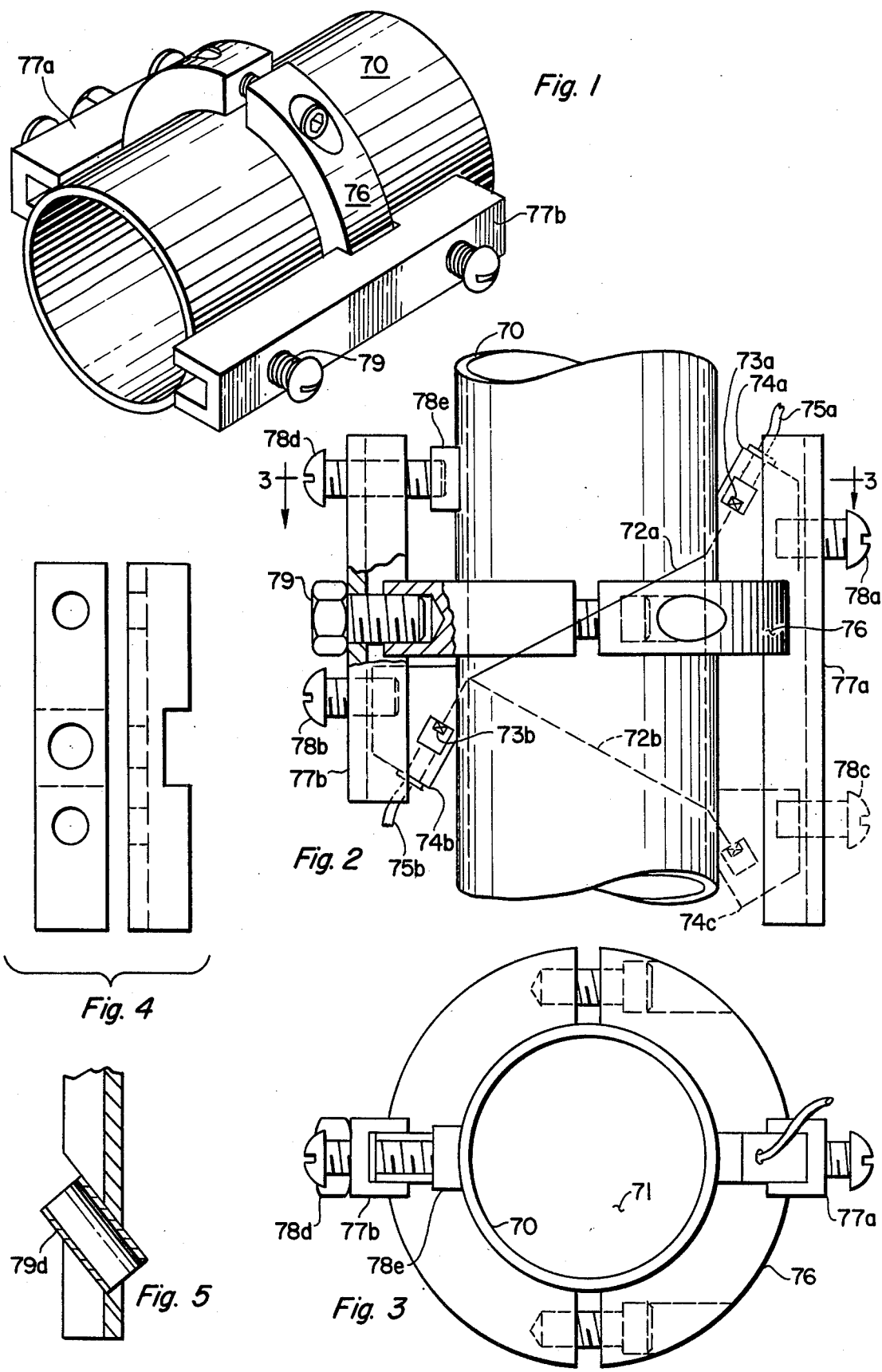

CLAMP-ON ULTRASONIC TRANSDUCER

BACKGROUND

This invention relates in general to ultrasonic measuring equipment and more particularly to a removable-clamp-on ultrasonic transducer for use in measuring fluid characteristics within a conduit. Ultrasonic measurement of the flow of a fluid within a conduit may utilize a variety of methods: contrapropagating transmission (upstream-downstream), reflection or Doppler, interaction with shed vortices, correlation, noise, etc. Many applications require that the transducers be coupled to the exterior of the conduit, without penetrating the wall.

In some cases, for example Doppler methods, only one transducer need be coupled to the pipe. In other cases two or more transducers may need to be coupled to the pipe. The transducers may need to be coupled on opposite sides, on the same side, or, for measurement of swirl, along the pipe at the ends of paths which may be rotated from one another.

Prior art transducer clamps generally consist of some sort of strapping arrangement attached directly to the transducer wedges. For example, hose clamps have been used, encircling both the pipe and the transducer wedge. Equivalently, turnbuckle and cable arrangements have been used. In either case, as the clamping means is tightened, the transducer's position varies, due to motion of the clamp. Prior art clamps do not provide for precise repositioning of the transducer.

Clamp-on ultrasonic transducers are known in the art. In one type of measurement problem it is desired to survey fluid conditions (particularly flow velocity) within different pipes at different locations about a plant using only one measurement device. In other applications the transducers may be considered dedicated to a particular site and will be bonded to the pipe with RTV rubber or epoxy. In the former case it is important that when the transducers are brought back to a particular site, they must be repositioned in the same location, or readings are unlikely to be repeatable despite the same flow velocity. Not only should the location and spacing of the transducers be repeatable, even the coupling conditions, e.g., pressure, should be repeatable, so as to not distort the pipe by different amounts on different occasions. One of these locations may be on a calibration flow loop. In the dedicated case, during the time that the couplant is curing, it is important that the transducers do not move. Furthermore, if dedicated transducers are being applied to two or more pipes whose contents are to be mixed in a controlled manner, e.g. pigments for a paint mixture, then it becomes important that installations on the several pipes are effected in a precise manner.

One problem associated with prior art transducers lies in the adjustment of the pressure between the transducer and the pipe or conduit. In general in the art the same adjustment elements that control the degree of tightness with which the clamp is fastened to the conduit, also controls the contact pressure of the transducing element. Too much pressure damages the element; too little and the clamp may slip either longitudinally or radially.

SUMMARY OF THE INVENTION

The present invention provides a clamp-on transducer where the clamping element has an interior surface formed to fit intimately with the exterior surface of the conduit. While the clamping element defines a plane transverse to the axis of the conduit and can be tightened very securely to the conduit, it does not itself carry the transducers on its inner surface and their degree of contact to the conduit can be independently adjusted. The clamping element has fixed to it one or more rigid channel members extending parallel to the axis of the conduit, each channel member carrying at least one transducing element, the geometry of the channel members being such that an oblique interrogation path lying in a plane parallel to the axis of the conduit is formed. The contact pressure of the transducing elements against the conduit may be independently adjusted.

The present invention includes the flexibility to control the transducer's position in a predetermined manner, or to allow the transducer to slide back and forth within a guide to obtain a position which is optimized with respect to coupling, maximum received signal or maximum refracted angle, for example. Predetermined positioning would be preferred for an application which is well established, or where a number of similar pipes are to be instrumented. The "tunable" positioning option might be preferred in an experimental situation.

It will be seen that the coupling pressure may be applied with a set screw or similar conventional fastener, or in a spring-loaded manner as with a spring-loaded plunger as is manufactured by the Vlier Corp. For operation over very wide temperature excursions, the spring-loaded coupling method may utilize inconel or other selected spring materials to maintain adequate coupling despite thermal expansion coefficient differences between pipe and clamp. However, preferred designs will incorporate materials such that thermal expansion differences will be minimized, when wide temperature excursions are anticipated. For example, pipe, clamp and screws may all be made of the same material. Clamps for glass pipe will typically be internally gasketed to avoid undue stresses on the pipe.

The split collar design will normally have a width W less than the pipe radius, so as to not interfere with placing transducers close enough to communicate along a contrapropagating transmission whose axial projection is D tan $\theta$ where D=pipe inside diameter and $\theta$=refracted angle given by Snell's Law. In correlation measurements the preferred spacing is between D/2 and 2D, so again W<D/2 is desirable.

The split collar will normally be built in two sections so it can be installed on existing pipe, or removed from a pipe, without opening the pipeline. To facilitate handling, the split collar may consist of hinged halves, including spring-loaded halves. However, when a pipeline is being built with the intention of subsequent use of clamp-on ultrasonic flowmeters, it would be possible to install slip-on collars which are C-shaped, that is, one-piece construction, with but a single tightening screw. Such collars could be slid along the pipe, but could not be removed without opening the pipe. Their advantage is improved security against theft. Also, they reduce the chances for human error, by preventing their inadvertent installation on the wrong pipe section.

DESCRIPTION OF THE DRAWINGS

In the drawing:

FIG. 1 is a generally perspective view of the transducer constructed in accordance with the principles of this invention;

FIG. 2 is a side elevation of the transducer shown in FIG. 1 with a portion broken away to show some interior detail;

FIG. 3 is a cross sectional view taken along the lines 3—3 of FIG. 2;

FIG. 4 is a detail view of the element 77b of FIG. 2; and

FIG. 5 is an illustration of an alternative configuration of a portion of FIG. 2.

DESCRIPTION OF PREFERRED EMBODIMENTS

Referring now to FIGS. 1 and 2, there is illustrated one preferred configuration of a "clamp-on" transducer arrangement. In this figure, the generally circular pipe or conduit 70 contains the fluid 71, generally liquid, whose flow velocity V is to be determined without penetrating the pipe. Accordingly, angle beam transducer assemblies are positioned on opposite sides of the pipe, consisting of wedges 74a, b containing transducer elements 73a, b. The elements are connected electrically via coaxial cables 75a, b to appropriate electronics provided, for example, from Panametrics, Inc., Waltham, Mass. under the designation Model 6000 Ultrasonic Flowmeter. The wedges are coupled acoustically by means of a liquid couplant, grease layer, resilient couplant such as an elastomeric film or soft, oxidation-resistant metal such as gold or platinum, or bonded, to the pipe 70. The transducers 73a, b communicate over the oblique path 72a, which may be a tilted diameter. The oblique path is controlled as follows. The two-piece split ring clamp 76 has a precision bore and is tightened around the pipe. Clamps of this type are commercially available from Ruland Manufacturing Co. of Watertown, Mass. for pipe sizes from about 1 to 3 inches, and for larger sizes, from Victaulic of So. Plainfield, N.J. To each half of the split ring, a channel 77a, b is rigidly and orthogonally connected. The connection may be by welding, as 77a is attached to its half of the ring, or by a bolt 79 tightened into a tapped hole in the ring. The milled groove or slot assures perpendicularity between the channel and the clamp, i.e., orthogonality between the plane of the clamp and the channel axis. Since the plane of the clamp is also perpendicular to the axis of the pipe, the channel axis and pipe axis are parallel. The clamp is rigid enough to substantially control the shape of the pipe in its vicinity, so the pipe remains circular, or is restored to a circular shape, despite minor eccentricities in pipe manufacture and despite coupling pressure which will be applied to the transducer assemblies. It will be understood that while a circular cross section cylinder is shown here as conduit 70, other generally cylindrical conduits having rectangular or elliptical cross sections may be used with a conforming shape in the clamp.

The channel 77a shown has an internal width machined approximately 0.1 mm larger than the width of the wedge 74a which it guides. Gib screws or shims (not shown) may be used to reduce play, if desired. The wedge 74a is pressed against the pipe exterior by turning adjustment screw 78a. Similarly wedge 74b is pressed by turning screw 78b. To balance this coupling force it may be desirable to use a second screw 78d which is shown pressing against a vee-grooved pad or nut 78e, which transfers the pressure to the pipe. In some cases both transducer assemblies will lie on the same side of the pipe. Thus in FIG. 2 there is shown in dashed lines, the wedge in alternative position 74c, pressed by screw 78c against the pipe to receive the zigzag bounce interrogation 72b.

The end view of FIG. 3 shows the channels diametrically opposed, and the transducers centered in their respective channel guides, thereby arranged to communicate along a tilted diameter. However the clamp and channels may be machined and/or fixtured prior to their rigid assembly to provide an off-diameter path for oblique interrogation. The main point is that the clamp is a precision fit to the pipe, such that within normal pipe or tubing tolerances, the clamp may be easily but reliably tightened in a fixed, stable position, and thereby serve as a platform or reference station. This platform, while removable, may in fact be left installed in a given location, while transducers may be installed, removed and later replaced in the channel guides. Since the cost of the split clamp is relatively small, normal industrial practice will usually dictate that the clamp remains in place as a "permanent" attachment to the pipe at a given measuring station. The transducers, however, being relatively costly, may frequently move from site to site if continuous measurements are not required at a given site, e.g. survey application. Prior art clamps generally were made as part of the transducer and so to remove the transducers the clamps had to be loosened or removed. Therefore when attempting to return to a given site and reproduce a given measuring condition, precision was unlikely to be obtained.

Another advantage of the present clamp design over prior art clamps is that whereas clamping bars provide a direct linkage for acoustic short circuit between the wedge pairs, the present arrangement described here introduces several impedance discontinuities including threaded and interrupted paths. If necessary for even further isolation, the screws shown pressing directly against the wedges may be isolated from said wedges by interposing either a single layer of acoustically dissimilar material such as Kapton or Teflon sheet, or several thin layers of alternately high and low acoustic impedance, e.g., steel, kapton or asbestoslike material, steel, etc.

The clamp and channel concept illustrated in FIG. 2 may be modified by the addition of drill bushings to serve as a fixture for field installation of transducer ports for wetted transducers. Drill bushing 79d for example is welded at 45° in the channel as shown in FIG. 5. Depending on pipe diameter, pipe material, wall thickness, etc. it may be desirable to reinforce the support of the channel (whether it contains a drill bushing or even if it contains only transducer wedges) by installing a second split ring clamp, thereby providing a second anchor for the channel. Similar to the channel with the drill bushing 79d, (but not shown) a channel can be installed with an oblique or radial clamping arrangement to serve as a welding fixture for field-installed transducer ports. Thus the same style split ring clamp may be used for one or more purposes related to ultrasonic flowmetering: basis for a precise clamp-on installation; basis for drilling and welding parts for wetted transducers; basis for bonding transducers or transducer fixtures at precise locations on the pipe.

The invention having been described it should be clear that various other embodiments and modifications are also intended to be covered by the appended claims.

I claim:

1. An ultrasonic transducer for measuring ultrasonic wave propagation in a medium contained within a generally cylindrical conduit comprising,
   a movable clamp having an inner periphery closely fitted to the outer periphery of said conduit in a plane transverse to the axis of said cylinder,
   means for securely fastening said clamp to said conduit thereby defining a plane transverse to said cylinder axis at a fixed point on said axis,
   a support member rigidly fixed to said clamp and extending in a direction parallel to said cylinder axis, said support member thereby defining a second plane parallel to said cylinder axis, and
   at least one transducer element removably carried on said support member for propagating ultrasonic waves into said conduit along an interrogation path within said medium.

2. Apparatus in accordance with claim 1 wherein said support member extends on either side of said clamp, said one transducer element positioned on said support member on one side of said clamp and further including a second transducing element positioned on said support member on the other side of said clamp at the opposite end of said interrogation path from said first transducing element.

3. Apparatus in accordance with claim 1 and further including coupling adjustment means for adjusting the pressure of contact between said transducing element and said conduit.

4. An ultrasonic transducer in accordance with claim 1 wherein the inner periphery of said removable clamp is provided with a gasket.

5. A transducer in accordance with claim 1 where in said transducing element may be carried at any of a plurality of positions along said support members.

6. An ultrasonic transducer for measuring ultrasonic wave propagation in a medium contained within a generally cylindrical conduit comprising:
   a removable clamp having an inner periphery closely fitted to the outer periphery of said conduit in a plane transverse to the axis of said cylinder;
   means for securely fastening said clamp to said conduit thereby defining a plane transverse to said cylinder axis at a fixed point on said axis;
   at least one support member rigidly fixed to said clamp and extending in a direction parallel to said cylinder axis, said support member thereby defining a second plane parallel to said cylinder axis;
   one or more transducer elements carried on said support member for propagating ultrasonic waves into said conduit along an interrogation path within said medium;
   coupling adjustment means carried on said support member for adjusting the pressure of contact between said transducer elements and said conduit, and force balancing means adapted to balance the coupling adjustment forces so generated.

* * * * *

UNITED STATES PATENT AND TRADEMARK OFFICE
CERTIFICATE OF CORRECTION

PATENT NO. : 4,286,470

DATED : September 1, 1981

INVENTOR(S) : Lawrence C. Lynnworth

It is certified that error appears in the above-identified patent and that said Letters Patent are hereby corrected as shown below:

On the title page
Assignee should read --Panametrics, Inc.--

Signed and Sealed this

Nineteenth Day of June 1984

[SEAL]

Attest:

GERALD J. MOSSINGHOFF

Attesting Officer

Commissioner of Patents and Trademarks